US010835541B2

(12) United States Patent
Maeda et al.

(10) Patent No.: US 10,835,541 B2
(45) Date of Patent: Nov. 17, 2020

(54) TABLET

(71) Applicant: Takeda Pharmaceutical Company Limited, Osaka (JP)

(72) Inventors: Arisa Maeda, Osaka (JP); Yuichi Sugiyama, Osaka (JP); Yoshihiro Uchiyama, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/748,446

(22) PCT Filed: Jul. 28, 2016

(86) PCT No.: PCT/JP2016/072109
§ 371 (c)(1),
(2) Date: Jan. 29, 2018

(87) PCT Pub. No.: WO2017/018473
PCT Pub. Date: Feb. 2, 2017

(65) Prior Publication Data
US 2018/0214460 A1 Aug. 2, 2018

(30) Foreign Application Priority Data

Jul. 30, 2015 (JP) .................................. 2015-151336

(51) Int. Cl.
*A61K 31/4439* (2006.01)
*A61K 31/616* (2006.01)
*A61K 9/28* (2006.01)
*A61K 9/24* (2006.01)

(52) U.S. Cl.
CPC ............ *A61K 31/616* (2013.01); *A61K 9/209* (2013.01); *A61K 9/282* (2013.01); *A61K 9/284* (2013.01); *A61K 9/2866* (2013.01); *A61K 31/4439* (2013.01); *A61K 9/2846* (2013.01)

(58) Field of Classification Search
CPC ...... A61K 9/209; A61K 9/284; A61K 9/2866; A61K 31/616; A61P 9/12; A61P 43/00
See application file for complete search history.

(56) References Cited

U.S. PATENT DOCUMENTS

| | | | |
|---|---|---|---|
| 9,050,368 B2 | 6/2015 | Phillips et al. | |
| 2002/0028240 A1 * | 3/2002 | Sawada | A61K 9/2031 424/472 |
| 2005/0249799 A1 * | 11/2005 | Jacob | A61K 9/0065 424/451 |
| 2005/0249811 A1 | 11/2005 | Plachetka | |
| 2008/0280944 A1 | 11/2008 | Fernstrom et al. | |
| 2009/0123390 A1 | 5/2009 | Hill | |
| 2010/0305163 A1 | 12/2010 | Yedurkar et al. | |
| 2011/0097401 A1 | 4/2011 | Phillips et al. | |
| 2013/0115291 A1 | 5/2013 | Misaki et al. | |
| 2013/0115292 A1 | 5/2013 | Misaki et al. | |

FOREIGN PATENT DOCUMENTS

| | | |
|---|---|---|
| CN | 105412038 | 3/2016 |
| EC | SP-05-6039 A | 9/2005 |
| EC | SP-05-6055 | 9/2005 |
| EC | SP-08-8545 | 6/2008 |
| EC | SP 11-010855 A | 3/2011 |
| EC | SP 11-010912 A | 4/2011 |
| JP | 2004-536809 A | 12/2004 |
| JP | 2014-533656 A | 12/2014 |
| WO | 97/25064 A1 | 7/1997 |
| WO | 00/01368 A1 | 1/2000 |
| WO | 02/22108 A1 | 3/2002 |
| WO | 02/098352 A2 | 12/2002 |
| WO | 2004089342 A2 | 10/2004 |
| WO | 2004101566 A1 | 11/2004 |
| WO | 2005/076987 A2 | 8/2005 |
| WO | 2007/064274 A1 | 6/2007 |
| WO | 2007064128 A1 | 6/2007 |
| WO | 2007125397 A2 | 11/2007 |
| WO | 2010013823 A2 | 2/2010 |
| WO | 2010024451 A1 | 3/2010 |
| WO | 2013/081177 A1 | 6/2013 |
| WO | 2013/101897 A2 | 7/2013 |

OTHER PUBLICATIONS

Wang et al, Current pharmacological management of gastroesophageal reflux disease, Hindawi Publication Corporation, vol. 2013.*
Takeda report on a new drug Application submitted for TAK-438, Feb. 28, 2014.*
International Search Report dated Sep. 27, 2016 in corresponding PCT Application PCT/JP2016/072109, 6 pages.
Kinoshita et al., "Problem and Prospect of PPI Treatment" Clinics in Gastroenterology, 18(3): 237-241(2015).
Iida et al., "Potassium-Competitive Acid Blocker—Proton Pump Inhibitor—Vonoprazan Fumarate Tablet" Journal of Japanese Society of Hospital Pharmacists, 51(6): 770-772 (2015).
Bliden, Kevin P., et al. "PA tablets: investigational compounds combining aspirin and omeprazole for cardioprotection." Future cardiology 9(6): 785-797 (2013).
Lehmann et al., "Fast disintegrating controlled release tablets from coated particles." Drugs Made in Germany 37(2): 53-60 (1994).

(Continued)

*Primary Examiner* — Mina Haghighatian
(74) *Attorney, Agent, or Firm* — Mintz Levin Cohn Ferris Glovsky and Popeo, P.C.; David G. Conlin; Joohee Lee

(57) ABSTRACT

The present invention provides a tablet showing high stability of the active ingredients (potassium-competitive acid blocker and acetylsalicylic acid) and stably and rapidly expressing the pharmacological effects of the active ingredients after administration.

The present invention provides a tablet containing an inner core and an outer layer, wherein the inner core is an enteric-coated tablet containing acetylsalicylic acid, and the outer layer contains a potassium-competitive acid blocker free of enteric coating.

13 Claims, No Drawings

(56) References Cited

OTHER PUBLICATIONS

Opposition filed by the Association of Pharmaceutical Laboratories (ALAFAR) on Feb. 7, 2019 in corresponding PCT Application No. PCT/JP2016/072109. Email receipt from Applicant included.
Supplemental European Search Report dated Feb. 4, 2019 in corresponding European Patent Application No. 16830578.7.
Takashi Kawai et al., "TAK-438 Versus Lansoprazole 15 mg for Secondary Prevention of Peptic Ulcers Associated with Non-Steroidal Anti-Inflammatory Drug (NSAID) Therapy: Results of a Phase 3 Trial", Gastroenterology, 2014, p. S-739. Aimi et al., "Effects of Omeprazole on Sleep Disturbance: Randomized Multicenter Double-Blind Pacebo-Controlled Trial".
Hori Yasunobu, et al. "A study comparing the antisecretory effect of TAK-438, a novel potassium-competitive acid blocker, with lansoprazole in animals." Journal of Pharmacology and Experimental Therapeutics 337.3 (2011): 797-804.
Garnock-Jones, Karly P. "Vonoprazan: first global approval." Drugs 75.4 (2015): 439-443.
Columbian Office Action dated Jun. 12, 2020 for Colombian Patent Application No. NC2018/0000991.
Zhigao Shao ed., Practical Dispensing Pharmacy, Southeast University Press, p. 201, published on Nov. 30, 2013, with English translation (4 pages).

\* cited by examiner

TABLET

CROSS REFERENCE TO RELATED APPLICATION

The present application is a U.S. National Stage Entry, pursuant to 35 U.S.C. § 371, of the International Patent Application No. PCT/JP2016/072109 filed Jul. 28, 2016, designating the United States, which also claims the benefit of priority to the Japanese Patent Application No. 2015-151336 filed Jul. 30, 2015. The entire contents of the aforementioned patent applications are incorporated herein for all purposes by this reference.

TECHNICAL FIELD

The present invention relates to a tablet containing a potassium-competitive acid blocker (hereinafter sometimes to be abbreviated as "P-CAB") and acetylsalicylic acid as active ingredients. More particularly, the present invention relates to a tablet superior in the stability of the aforementioned active ingredients, and expressing pharmacological effects stably and rapidly after administration.

BACKGROUND OF THE INVENTION

It sometimes occurs that low dose acetylsalicylic acid administered to suppress thrombus and/or embolization (antiplatelet therapy) in cerebrovascular and circulatory diseases induces gastric ulcer or duodenal ulcer. Since discontinuation of administration of acetylsalicylic acid may result in thrombus and/or embolization, it is considered important to continue administration of low dose acetylsalicylic acid while suppressing the onset of ulcer.

While acetylsalicylic acid is also known as a non-steroidal anti-inflammatory drug (NSAIDs), and mainly used for the treatment of pain, fever and inflammation, non-steroidal anti-inflammatory drug may cause gastric ulcer or duodenal ulcer. Particularly, in the treatment of rheumatoid arthritis, osteoarthritis and the like, discontinuation of administration of non-steroidal anti-inflammatory drug may be difficult, since it markedly degrades the quality of life (QOL). Therefore, it is considered important to continue administration of non-steroidal anti-inflammatory drug while suppressing the onset of ulcer.

On the other hand, since proton pump inhibitors of benzimidazole compound such as lansoprazole, omeprazole and the like (hereinafter sometimes to be abbreviated as "PPI") have a gastric acid secretion-inhibitory action, a gastric mucosa-protective action and the like, and therefore, have been widely used as therapeutic agents for peptic ulcer and the like. In recent years, potassium-competitive acid blockers have been attracting attention as medicaments that effectively suppress secretion of gastric acid, and improve instability under acidic conditions, variations in effects based on metabolic enzyme polymorphisms and interaction between drugs, which are the problems of known proton pump inhibitors. Particularly, as for vonoprazan preparations, in Japan, the efficacy of "inhibition of recurrence of gastric ulcer or duodenal ulcer by administration of low dose acetylsalicylic acid" and "suppression of recurrence of gastric ulcer or duodenal ulcer by administration of non-steroidal anti-inflammatory drug" was approved and clinical effects have been demonstrated for suppression of the onset of gastric ulcer or duodenal ulcer caused by administration of acetylsalicylic acid.

Patent document 1 (WO 97/25064) discloses a pharmaceutical dosage form for oral administration containing an acid-susceptible proton pump inhibitor protected with an enteric coating layer, at least one kind of non-steroidal anti-inflammatory drug, and a pharmaceutically acceptable excipient when desired, which is characterized by being a fixed unit dosage form.

Patent document 2 (WO 2007/064274) discloses an oral pharmaceutical dosage form comprising, as active ingredients, an acid susceptible proton pump inhibitor together with acetyl salicylic acid or a derivative thereof and further an optionally pharmaceutically acceptable excipient, which is characterized in that the dosage form is in the form of an oral fixed combination dosage form comprising a group of separate physical units comprising the acid susceptible proton pump inhibitor and one or more other separate physical units comprising the acetyl salicylic acid or a derivative thereof, and wherein at least the proton pump inhibitor is protected by an enteric coating layer.

Patent document 3 (WO 2005/076987) discloses a pharmaceutical composition comprising: (a) a therapeutically effective amount of at least one acid labile proton pump inhibitor; (b) at least one buffering agent in an amount sufficient to increase gastric fluid pH to a pH that prevents acid degradation of at least some of the proton pump inhibitor in the gastric fluid; and (c) a therapeutically effective amount of at least one non-steroidal anti-inflammatory drug.

Patent document 4 (WO 2002/098352) discloses a pharmaceutical composition in unit dose form suitable for oral administration to a patient, comprising: (a) an acid inhibitor present in an amount effective to raise the gastric pH of said patient to at least 3.5 upon the administration of one or more of said unit dosage forms; (b) a non-steroidal anti-inflammatory drug in an amount effective to reduce or eliminate pain or inflammation in said patient upon administration of one or more of said unit dosage forms; and wherein said unit dosage form provides for the coordinated release of said acid inhibitor followed by said non-steroidal anti-inflammatory drug, that is, the acid inhibitor is released earlier, the pH in the stomach raised to at least 3.5 and the non-steroidal anti-inflammatory drug covered with enteric coating is released.

Patent document 5 (WO 2013/081177) discloses a dry coated tablet having an inner core and an outer layer, wherein the inner core is an enteric-coated tablet containing acetylsalicylic acid and the outer layer is an enteric fine granule containing a proton pump inhibitor.

Furthermore, vonoprazan and acetylsalicylic acid have already been commercially available each as a single agent. However, tablets containing both P-CAB such as vonoprazan and the like and acetylsalicylic acid are not known.

DOCUMENT LIST

Patent Documents patent document 1: WO 97/25064
patent document 2: WO 2007/064274
patent document 3: WO 2005/076987
patent document 4: WO 2002/098352
patent document 5: WO 2013/081177

SUMMARY OF THE INVENTION

Problems to be Solved by the Invention

It is clinically extremely highly useful to provide a preparation containing both P-CAB and acetylsalicylic acid as active ingredients (combination agent, also called compounding agent). However, practicalization of a preparation containing plural active ingredients is not easy as compared to preparations containing a single active ingredient. For example, the composition of the preparation needs to be controlled such that the dissolution rate of the active ingredient is optimized upon practicalization of the preparation, since the dissolution rate of the active ingredient from the preparation can influence the time-course efficacy profile after administration. In the case of a combination agent, however, the dissolution rate of each active ingredient needs to be optimized, and pharmaceutical difficulty is high. In addition, it is also necessary to suppress adverse effects caused by the interaction of plural active ingredients contained in the combination agent, for example, degradation of preservation or chemical stability (decomposition over time and reduction of activity of active ingredients and the like), decrease of dissolution stability (change of active ingredient dissolution pattern over time and the like) and the like.

Furthermore, the development of a tablet that can be taken easily while maintaining the handling convenience, which is the characteristics of tablet, is desired along with the aging of the population and/or change of life environment.

Means of Solving the Problems

The present inventors have conducted intensive studies in an attempt to solve the above-mentioned problems and found that an enteric-coated tablet containing acetylsalicylic acid as an inner core and containing P-CAB in an outer layer thereof shows high stability of the active ingredients (acetylsalicylic acid and P-CAB), and that pharmacological effects of the active ingredients are stably and rapidly expressed after administration, which resulted in the completion of the present invention.

That is, the present invention provides

[1] a tablet comprising an inner core and an outer layer, wherein the inner core is an enteric-coated tablet comprising acetylsalicylic acid, and the outer layer comprises a potassium-competitive acid blocker free of enteric coating,
[2] the tablet of the aforementioned [1] wherein the potassium-competitive acid blocker is 1-[5-(2-fluorophenyl)-1-(pyridin-3-ylsulfonyl)-1H-pyrrol-3-yl]-N-methylmethanamine (vonoprazan) or a salt thereof,
[3] the tablet of the aforementioned [1] wherein the content of acetylsalicylic acid is 70 mg-120 mg per one table,
[4] the tablet of the aforementioned [1] comprising an intermediate layer between the inner core and the outer layer,
[5] the tablet of the aforementioned [4] wherein the intermediate layer comprises a water-soluble polymer,
[6] the tablet of the aforementioned [5] wherein the water-soluble polymer is one or more kinds selected from the group consisting of hydroxypropylcellulose, poly(vinyl alcohol) and hydroxypropylmethylcellulose,
[7] the tablet of the aforementioned [1] wherein the outer layer further comprises an organic acid,
[8] the tablet of the aforementioned [7] wherein the organic acid is fumaric acid,
[9] the tablet of any of the aforementioned [1] to [8] further comprising a coating layer on the outside of the outer layer,
[10] the tablet of the aforementioned [9] wherein the coating layer comprises a water-soluble polymer,
[11] the tablet of the aforementioned [10] wherein the water-soluble polymer is one or more kinds selected from the group consisting of hydroxypropylcellulose, poly(vinyl alcohol) and hydroxypropylmethylcellulose,
[12] the tablet of the aforementioned [1] wherein the enteric coating layer in the inner core comprises methacrylic acid copolymer LD and ethyl acrylate-methyl methacrylate copolymer,
[13] the tablet of the aforementioned [12] wherein the content ratio of methacrylic acid copolymer LD and ethyl acrylate-methyl methacrylate copolymer (methacrylic acid copolymer LD:ethyl acrylate-methyl methacrylate copolymer) is 85:15-95:5 in a weight ratio, and
[14] a method for producing the tablet of the aforementioned [1] comprising spraying a solution or suspension comprising a potassium-competitive acid blocker on an enteric-coated tablet comprising acetylsalicylic acid (when the aforementioned enteric-coated tablet further comprises an intermediate layer, enteric-coated tablet comprising acetylsalicylic acid and after coating the intermediate layer).

Effect of the Invention

Since the tablet of the present invention contains (1) P-CAB having a strong acid secretion suppressive action and (2) acetylsalicylic acid useful as a prophylactic and/or therapeutic agent for cerebrovascular or circulatory diseases, for example, a thrombus and/or embolization inhibitor for angina pectoris (chronic stable angina pectoris, unstable angina pectoris), myocardial infarction; a prophylactic and/or therapeutic agent for ischemic cerebrovascular disorder (transient ischemic attack (TIA), cerebral infarction); a thrombus and/or embolization inhibitor used after coronary-artery bypass surgery (CABG) or percutaneous transluminal coronary angioplasty (PTCA); or a prophylactic and/or therapeutic agent for Kawasaki disease (including cardiovascular sequelae due to Kawasaki disease), the tablet of the present invention can be administered for the purpose of treating gastric ulcer or duodenal ulcer or suppressing the onset of these, while continuing the administration of acetylsalicylic acid.

In addition, since acetylsalicylic acid can also be used as one kind of non-steroidal anti-inflammatory drug mainly for the treatment of pain, fever and inflammation, the tablet of the present invention can be administered for the purpose of treating gastric ulcer or duodenal ulcer or suppressing the onset of these, while continuing the administration of a non-steroidal anti-inflammatory drug.

The tablet of the present invention can be easily taken while maintaining the convenience of handling.

Furthermore, the tablet of the present invention is superior in the preservation stability and dissolution property of the active ingredients (acetylsalicylic acid and P-CAB), and the pharmacological effect of the active ingredient is expressed stably and rapidly after administration of the tablet of the present invention.

DETAILED DESCRIPTION OF THE INVENTION

The present invention is explained in detail in the following.

The tablet of the present invention has an inner core and an outer layer and is characterized in that the inner core is an "enteric-coated tablet containing acetylsalicylic acid" and the outer layer contains "P-CAB free of enteric coating".

(1) "Enteric-Coated Tablet Containing Acetylsalicylic Acid"

The "enteric-coated tablet containing acetylsalicylic acid" in the tablet of the present invention contains 1) acetylsalicylic acid, 2) optionally added additive, and 3) enteric coating component and constitutes the inner core of the tablet.

The "enteric-coated tablet containing acetylsalicylic acid" can be produced by mixing 1) acetylsalicylic acid and 2) an optionally added additive and tableting the mixture to give "core tablet containing acetylsalicylic acid", and covering same with 3) an enteric coating component.

Acetylsalicylic acid may be produced by a production method known per se, for example, by reacting phenol with carbon dioxide and sodium hydroxide under a high-temperature and a high-pressure to form a disodium salt of salicylic acid, neutralizing same with dilute sulfuric acid, reacting same with acetic anhydride for acetylation and the like and used. In addition, products provided by each company can also be used.

As used herein, "coating" is not limited to covering the whole surface of the target to be coated (core tablet containing acetylsalicylic acid). It also means not only partially covering same, covering when the target to be coated adsorbs or absorbs an enteric coating component or covering the core tablet in the inner core, but also covering a single active ingredient of acetylsalicylic acid or fine granules or granules containing same to give an enteric-coated tablet.

The content of acetylsalicylic acid in the tablet of the present invention is generally about 70-about 400 mg per one tablet. As the non-steroidal anti-inflammatory drug, the content of acetylsalicylic acid in the tablet of the present invention is generally about 250-about 400 mg per one tablet when mainly aiming at a treatment of pain, fever or inflammation.

On the other hand, when mainly aiming at suppression of thrombus and/or embolization (antiplatelet therapy) and the like in cerebrovascular and circulatory diseases, the content of acetylsalicylic acid in the tablet of the present invention is generally about 70 mg-about 120 mg (preferably about 100 mg) per one tablet.

In addition, the content of acetylsalicylic acid is generally about 10-about 60 wt % relative to the total amount of the tablet of the present invention (i.e., final tablet containing outer layer and the like).

As the aforementioned "optionally added additive", excipient, disintegrant, fluidizer, binder, surfactant, lubricant and the like are used.

Examples of the aforementioned "excipient" include lactose, sucrose, D-mannitol, starch, cornstarch, crystalline cellulose, light anhydrous silicic acid and the like. One kind of these excipients may be used singly or two or more kinds thereof may also be used in combination. The content of the "excipient" is generally about 5-about 30 wt %, preferably about 10-about 20 wt %, relative to the total amount of "enteric-coated tablet containing acetylsalicylic acid".

Examples of the aforementioned "disintegrant" include carmellose, croscarmellose sodium, crystalline cellulose, pregelatinized starch, gelatin, low-substituted hydroxypropylcellulose and the like. One kind of these may be used singly or two or more kinds thereof may also be used in combination. Particularly, from the aspect of the disintegration property of the enteric-coated tablet containing acetylsalicylic acid and improvement of the stability of acetylsalicylic acid, carmellose is preferably used. The content of the "disintegrant" is generally about 1-about 20 wt %, preferably about 1-about 10 wt %, relative to the total amount of the "enteric-coated tablet containing acetylsalicylic acid".

Examples of the aforementioned "fluidizer" include light anhydrous silicic acid, hydrated silicon dioxide, talc, stearic acid and the like. One kind of these may be used singly or two or more kinds thereof may also be used in combination. The content of the "fluidizer" is generally 0-about 10 wt % relative to the total amount of the "enteric-coated tablet containing acetylsalicylic acid".

Examples of the aforementioned "binder" include hydroxypropylcellulose, cornstarch, hydroxypropylmethylcellulose, crystalline cellulose, pregelatinized starch, polyvinylpyrrolidone, gum arabic powder, gelatin, pullulan, low-substituted hydroxypropylcellulose and the like. One kind of these may be used singly or two or more kinds thereof may also be used in combination. The content of the "binder" is generally 0-about 10 wt % relative to the total amount of the "enteric-coated tablet containing acetylsalicylic acid".

Examples of the aforementioned "surfactant" include sodium lauryl sulfate, polyoxyethylene-polyoxypropyleneglycol, polysorbate 80 and the like. One kind of these may be used singly or two or more kinds thereof may also be used in combination.

Examples of the aforementioned "lubricant" include hydrogenated oil, sodium lauryl sulfate, stearic acid, polysorbate 80 and the like. One kind of these may be used singly or two or more kinds thereof may also be used in combination.

Here, since lubricants such as stearic acid, magnesium stearate, calcium stearate, sodium stearyl fumarate and the like show poor compatibility with acetylsalicylic acid, the core tablet in the inner core of the tablet of the present invention preferably does not contain the aforementioned lubricants such as stearic acid, magnesium stearate and the like.

As the aforementioned additive, excipient, disintegrant, binder and the like are preferably used.

Mixing of acetylsalicylic acid and an additive is uniformly performed using a acetylsalicylic acid powder, or a premix product of acetylsalicylic acid and an excipient (e.g., dry granulation product of acetylsalicylic acid and cornstarch (acetylsalicylic acid:cornstarch=90:10 (weight ratio))). To avoid tableting trouble and poor flowability, it is desirable to uniformly mix acetylsalicylic acid granulation product having a large particle size and superior in flowability with other additives and tablet same to produce a core tablet containing acetylsalicylic acid.

The "mixing" of the acetylsalicylic acid and additive is performed by a mixing method generally used, for example, mixing, kneading, granulation and the like. The "mixing" is performed using an apparatus such as vertical granulator VG10 (manufactured by POWREX), universal kneader (manufactured by HATA TEKKOSHO CO., LTD.), fluid bed granulator LAB-1, FD-3S, FD-WSG-60 (manufactured by POWREX), V-type mixer, tumbler mixer and the like.

The "tableting" is performed by single punch tabletting using Autograph (manufactured by Shimadzu Corporation) and the like, or a rotary tableting machine (manufactured by Kikusui Seisakusho Ltd., or manufactured by HATA TEKKOSHO CO., LTD.) and the like.

As the "enteric coating component" for covering the "core tablet containing acetylsalicylic acid", water-dispersible enteric polymer bases such as cellulose acetate phthalate (CAP (trade name; Aquateric manufactured by FMC) and the like), hydroxypropylmethylcellulosephthalate (HP-55 (trade name; manufactured by Shin-Etsu Chemical Co., Ltd.) and the like), hydroxymethylcelluloseacetatesuccinate, methacrylic acid copolymer (e.g., methacrylic acid copolymer LD (Eudragit L30D-55 (trade name; manufactured by Evonik), Kollicoat MAE30DP (trade name; manufactured by BASF), POLYQUID PA30 (trade name; manufactured by Sanyo Chemical Industries, Ltd.) and the like) and the like), carboxymethylethylcellulose, shellac and the like; sustained-release substrates such as methacrylate copolymer (e.g., ethyl acrylate-methyl methacrylate copolymer (Eudragit NE30D (trade name; manufactured by Evonik) and the like), aminoalkylmethacrylate copolymer RS (Eudragit RL30D (trade name; manufactured by Evonik), Eudragit RS30D (trade name; manufactured by Evonik) and the like) and the like) and the like; water-soluble polymers such as ethanol-soluble water-soluble polymer (e.g., cellulose derivative such as hydroxypropylcellulose (hereinafter sometimes to be indicated as HPC) and the like, polyvinylpyrrolidone and the like), ethanol-insoluble water-soluble polymer (e.g., cellulose derivative such as hydroxypropylmethylcellulose (hereinafter sometimes to be indicated as HPMC), methylcellulose, carmellose sodium and the like, sodium polyacrylate, poly(vinyl alcohol), sodium alginate, guar gum and the like) and the like; plasticizers such as triethyl citrate, polyethylene glycol, acetylated monoglyceride, triacetine, castor oil and the like, and the like are used. One kind of these may be used singly or two or more kinds thereof may also be used in combination.

As the aforementioned "water-dispersible enteric polymer base", methacrylic acid copolymer such as methacrylic acid copolymer LD and the like is preferable. The content of the "water-dispersible enteric polymer base" is generally about 3-about 20 wt % relative to the total amount of "enteric-coated tablet containing acetylsalicylic acid".

As the aforementioned "sustained-release substrate", methacrylate copolymer such as ethyl acrylate-methyl methacrylate copolymer and the like is preferable. The content of the "sustained-release substrate" is generally about 0.3-about 1.0 wt % relative to the total amount of the "enteric-coated tablet containing acetylsalicylic acid". The content of the "sustained-release substrate" is generally about 5-about 30 parts by weight, preferably about 5-about 15 parts by weight, per 100 parts by weight of the water-dispersible enteric polymer base.

As the aforementioned "plasticizer", triethyl citrate and the like are preferable. The content of the "plasticizer" is generally about 0.5-about 3.0 wt % relative to the total amount of the "enteric-coated tablet containing acetylsalicylic acid". The content of the "plasticizer" is preferably about 10-about 30 parts by weight per 100 parts by weight of the water-dispersible enteric polymer base.

As the enteric coating component constituting the enteric coating layer of the "enteric-coated tablet containing acetylsalicylic acid", a coating agent containing a water-dispersible enteric polymer base and a sustained-release substrate is preferably used. Particularly, a coating agent of a mixture of a methacrylic acid copolymer such as methacrylic acid copolymer LD and the like, and a methacrylate copolymer such as ethyl acrylate-methyl methacrylate copolymer and the like at a given rate is desirably used.

For example, a preferable containing ratio of the methacrylic acid copolymer such as methacrylic acid copolymer LD and the like, and the methacrylate copolymer such as ethyl acrylate-methyl methacrylate copolymer and the like (methacrylic acid copolymer (particularly methacrylic acid copolymer LD):methacrylate copolymer (particularly ethyl acrylate-methyl methacrylate copolymer)) is preferably about 85:15-about 95:5, particularly about 9:1, in weight ratio.

The aforementioned "enteric coating component" may contain various additives such as surfactant, lubricant, pH adjuster and the like in addition to the aforementioned water-dispersible enteric polymer base, sustained-release substrate, water-soluble polymer and plasticizer.

Examples of the aforementioned "surfactant" include polysorbate (e.g., polysorbate 80), polyoxyethylene-polyoxypropylene copolymer, sodium lauryl sulfate and the like, particularly preferably polysorbate and sodium lauryl sulfate. The content of the "surfactant" is generally about 1-about 5 wt % relative to the total amount of the enteric coating component.

Examples of the aforementioned "lubricant" include talc, glycerol monostearate and the like, particularly preferably glycerol monostearate. The content of the "lubricant" is generally about 1-about 30 wt % relative to the total amount of the enteric coating components.

Examples of the aforementioned "pH adjuster" include citric anhydride. The content of the "pH adjuster" is generally 0-about 2 wt % relative to the total amount of the enteric coating components.

The ratio of the enteric coating component to the "core tablet containing acetylsalicylic acid" can be selected from the range capable of controlling the acid resistance of acetylsalicylic acid and dissolution property. For example, it is generally about 3-about 30 parts by weight, preferably about 5-about 20 parts by weight, per 100 parts by weight of the aforementioned core tablet.

The "enteric coating layer" to be formed on the "core tablet containing acetylsalicylic acid" may be formed with plural layers, and the combination of various coating layers other than the enteric coating layer such as coating layer for undercoating and the like may be appropriately selected as necessary.

The aforementioned "enteric-coated tablet containing acetylsalicylic acid" can be produced by covering a "core tablet containing acetylsalicylic acid" with an "enteric coating component" by a known coating method.

While the aforementioned coating method is not particularly limited, for example, it can be performed by spraying a coating solution containing the enteric coating components on a core tablet by using a coating machine such as a film coating machine and the like.

As the aforementioned coating solution for enteric coating, for example, a mixture of the enteric coating components such as the aforementioned water-dispersible enteric polymer base, sustained-release substrate, water-soluble polymer, plasticizer, surfactant, lubricant, pH adjuster and the like is used. The mixture may be a solution or dispersion, and can be prepared using water or an organic solvent such as ethanol and the like, or a mixed solution of these. The concentration of the polymer components such as water-dispersible enteric polymer base, sustained-release substrate and water-soluble polymer and the like in the mixture is generally about 0.1-about 50 wt %, preferably about 5-about 30 wt %.

Furthermore, the tablet of the present invention optionally has an intermediate layer between the inner core and the outer layer. The "intermediate layer" is a coating layer formed as necessary on the outside of the enteric coating layer of the "enteric-coated tablet containing acetylsalicylic acid" in the inner core.

In the tablet of the present invention, the aforementioned intermediate layer contains a water-soluble polymer.

Examples of the "water-soluble polymer" contained in the intermediate layer include ethanol-soluble water-soluble polymer (e.g., cellulose derivative such as hydroxypropylcellulose (HPC) and the like, polyvinylpyrrolidone and the like), ethanol-insoluble water-soluble polymer (e.g., cellulose derivative such as hydroxypropylmethylcellulose (HPMC), methylcellulose, carmellose sodium and the like, sodium polyacrylate, poly(vinyl alcohol), sodium alginate, guar gum and the like) and the like. One kind of these water-soluble polymers may be used singly or two or more kinds thereof may also be used in combination.

For the object of the present invention, as a water-soluble polymer contained in the intermediate layer, one or more kinds selected from the group consisting of hydroxypropylcellulose, poly(vinyl alcohol) and hydroxypropylmethylcellulose are preferably used.

The content of the "water-soluble polymer" in the intermediate layer is generally about 70-about 95 wt %.

In the tablet of the present invention, the intermediate layer may contain a lubricant and the like in addition to the aforementioned "water-soluble polymer".

Examples of the aforementioned "lubricant" include talc, magnesium stearate, sucrose fatty acid ester, glycerol fatty acid ester, polyethylene glycol, stearic acid, hydrogenated oil and the like.

The content of the lubricant in the intermediate layer is generally about 5-about 30 wt %.

The intermediate layer can be coated on the outside of the enteric coating layer of the "enteric-coated tablet containing acetylsalicylic acid" in the inner core by a general coating method. For example, a method for spraying a film coating solution containing the aforementioned water-soluble polymer and a lubricant on the surface of the aforementioned enteric-coated tablet by using a film coating machine, a method for spray coating by a fluid bed coating method and the like, and the like can be used.

When the tablet of the present invention has an "intermediate layer" between the inner core and the outer layer, the moisture-proof effect of the inner core is reinforced and therefore, improvement of the preservation stability of the preparation is expected.

In the present specification, the "enteric-coated tablet containing acetylsalicylic acid" and "enteric-coated tablet containing acetylsalicylic acid having an intermediate layer" are sometimes to be referred to as the "inner core tablet".

(2) "Outer Layer Containing P-CAB Free of Enteric Coating"

(2)-1: Potassium-Competitive Acid Blocker (P-CAB)

In the present invention, as P-CAB, different from previous proton pump inhibitors (PPI), a compound stable to acid, reversibly inhibiting $H^+,K^+$-ATPase (proton pump) in the final stage of acid secretion in stomach wall cells in a competitive manner with potassium ion without requiring activation by an acid, and showing an acid secretion suppressive action, or a salt thereof can be mentioned.

As such compound, the following can be mentioned.

[A] Compounds disclosed in WO 2006/036024, WO 2007/026916, WO 2008/108380, WO 2010/024451 and WO 2010/110378, for example, 1-{5-(2-fluorophenyl)-1-[(6-methylpyridin-3-yl)sulfonyl]-1H-pyrrol-3-yl}-N-methylmethanamine, 1-[4-fluoro-5-phenyl-1-(pyridin-3-ylsulfonyl)-1H-pyrrol-3-yl]-N-methylmethanamine, N-methyl-1-[5-(4-methyl-3-thienyl)-1-(pyridin-3-ylsulfonyl)-1H-pyrrol-3-yl]methanamine, 1-[5-(2-fluoropyridin-3-yl)-1-(pyridin-3-ylsulfonyl)-1H-pyrrol-3-yl]-N-methylmethanamine, 1-[5-(2-fluorophenyl)-1-(pyridin-3-ylsulfonyl)-1H-pyrrol-3-yl]-N-methylmethanamine (vonoprazan), N-methyl-1-[5-(2-methylphenyl)-1-(pyridin-3-ylsulfonyl)-1H-pyrrol-3-yl]methanamine, 1-{4-fluoro-5-(2-fluoropyridin-3-yl)-1-[(4-methylpyridin-2-yl)sulfonyl]-1H-pyrrol-3-yl}-N-methylmethanamine, 1-{4-fluoro-5-(2-fluoropyridin-3-yl)-1-[(5-fluoropyridin-2-yl)sulfonyl]-1H-pyrrol-3-yl}-N-methylmethanamine, 1-{4-fluoro-5-(2-fluoropyridin-3-yl)-1-[(4-methoxypyridin-2-yl)sulfonyl]-1H-pyrrol-3-yl}-N-methylmethanamine, 1-{4-fluoro-5-(2-fluoropyridin-3-yl)-1-[(5-fluoropyridin-3-yl)sulfonyl]-1H-pyrrol-3-yl}-N-methylmethanamine, 1-{4-fluoro-5-(2-fluoropyridin-3-yl)-1-[(6-methylpyridin-3-yl)sulfonyl]-1H-pyrrol-3-yl}-N-methylmethanamine, 1-{5-[(4-fluorophenyl)sulfonyl]-1-(2-fluoropyridin-3-yl)-1H-pyrazol-3-yl}-N-methylmethanamine, 1-{1-(2-fluoropyridin-3-yl)-5-[(4-methoxyphenyl)sulfonyl]-1H-pyrazol-3-yl}-N-methylmethanamine, 1-{1-(2-fluoropyridin-3-yl)-5-[(3-methylphenyl)sulfonyl]-1H-pyrazol-3-yl}-N-methylmethanamine, 3-({1-(2-fluoropyridin-3-yl)-3-[(methylamino)methyl]-1H-pyrazol-5-yl}sulfonyl)benzonitrile, or a salt thereof (hereinafter a group of these compounds is abbreviated as "Group A");

[B] 5,6-dimethyl-2-(4-fluorophenylamino)-4-(1-methyl-1,2,3,4-tetrahydroisoquinolin-2-yl)pyrimidine (revaprazan (YH1885)) or a salt thereof;

[C] compound disclosed in EP-A-1784404, for example, 1-benzyl-7-(1,2,3,4-tetrahydroisoquinolin-2-yl)-2,3-dimethyl-1H-pyrrolo[2,3-c]pyridine, 1-(3-fluorobenzyl)-7-(1,2,3,4-tetrahydroisoquinolin-2-yl)-2,3-dimethyl-1H-pyrrolo[2,3-c]pyridine, YH4808, or a salt thereof;

[D] compounds disclosed in EP-A-2452680 or U.S. Pat. No. 8,648,080, for example, (S)-(-)-4-[(5,7-difluoro-3,4-dihydro-2H-chromen-4-yl)oxy]-N,N,2-trimethyl-1H-benzimidazole-6-carboxamide, (-)-1-(2-methoxyethyl)-N,N,2-trimethyl-8-phenyl-1,6,7,8-tetrahydrochromeno[7,8-d]imidazole-5-carboxamide, 8-[{2,6-dimethylbenzyl}amino]-N-[2-hydroxyethyl]-2,3-dimethylimidazo[1,2-a]pyridine-6-carboxamide, 7-{[(4S)-5,7-difluoro-3,4-dihydro-2H-chromen-4-yl]oxy}-N,N,2-trimethyl-1H-benzimidazole-5-carboxamide (tegoprazan (RQ-4)), RQ-774, or a salt thereof;

[E] 7-(4-fluorobenzyloxy)-2,3-dimethyl-1-{[(1S,2S)-2-methylcyclopropyl]methyl}-1H-pyrrolo[2,3-d]pyridazine (CS-526) or a salt thereof, and the like.

Of those mentioned above, 1-[5-(2-fluorophenyl)-1-(pyridin-3-ylsulfonyl)-1H-pyrrol-3-yl]-N-methylmethanamine (vonoprazan), 5,6-dimethyl-2-(4-fluorophenylamino)-4-(1-methyl-1,2,3,4-tetrahydroisoquinolin-2-yl)pyrimidine (revaprazan (YH1885)), YH4808, 7-{[(4S)-5,7-difluoro-3,4-dihydro-2H-chromen-4-yl]oxy}-N,N,2-trimethyl-1H-benzimidazole-5-carboxamide (tegoprazan (RQ-4)), RQ-774, 7-(4-fluorobenzyloxy)-2,3-dimethyl-1-{[(1S,2S)-2-methylcyclopropyl]methyl}-1H-pyrrolo[2,3-d]pyridazine (CS-526) or a salt thereof is preferable, particularly, 1-[5-(2-fluorophenyl)-1-(pyridin-3-ylsulfonyl)-1H-pyrrol-3-yl]-N-methylmethanamine (vonoprazan) or a salt thereof (particularly, vonoprazan fumarate) is preferable.

Examples of the aforementioned "salt" include metal salts, ammonium salt, salts with organic bases, salts with inorganic acids, salts with organic acids, salts with basic or acidic amino acids and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salts with inorganic acids include salts with hydrochloric acid, hydrobromic acid, nitric acid, sulfuric acid, phosphoric acid and the like.

Preferable examples of the salts with organic acids include salts with adipic acid, ascorbic acid, benzoic acid, oleic acid, succinic acid, acetic acid, tartaric acid, sorbic acid, fumaric acid, lactic acid, maleic acid, malonic acid, citric anhydride, maleic anhydride, phthalic acid, phthalic anhydride, malic acid, formic acid, trifluoroacetic acid, oxalic acid, methanesulfonic acid, benzenesulfonic acid, p-toluenesulfonic acid and the like.

Preferable examples of the salts with basic amino acids include salts with arginine, lysine, ornithine and the like, and preferable examples of the salts with acidic amino acids include salts with aspartic acid, glutamic acid and the like.

(2)-2: "Outer Layer Containing P-CAB Free of Enteric Coating"

P-CAB mentioned above is stable to acid. To rapidly express efficacy thereof, P-CAB contained in the outer layer is preferably free of an enteric coating in the tablet of the present invention.

In the tablet of the present invention, P-CAB free of an enteric coating is contained in the outer layer. The aforementioned "outer layer" is formed outside the enteric-coated tablet containing acetylsalicylic acid in the inner core (when intermediate layer is present between inner core and outer layer, it is formed outside the intermediate layer). The outer layer may contain an additive besides P-CAB.

The content of P-CAB is generally about 1-about 70 wt %, preferably about 3-about 70 wt %, in the "outer layer", and generally about 3-about 20 wt %, preferably, about 5-about 10 wt %, relative to the total amount of the tablet of the present invention.

Examples of the aforementioned "additive" include "excipient" such as water-soluble sugar alcohol and the like. The aforementioned "water-soluble sugar alcohol" means sugar alcohol that requires, when 1 g thereof is added to water and dissolved within about 30 min by vigorously shaking the mixture for 30 sec at 20° C. every 5 min, less than 30 mL of water for dissolution.

Examples of the "water-soluble sugar alcohol" include sorbitol, mannitol, maltitol, reduced starch saccharides, xylitol, reduced paratinose, erythritol and the like. One kind of these may be used singly or two or more kinds (preferably 2-3 kinds) thereof may also be used as a mixture at an appropriate ratio.

As the "water-soluble sugar alcohol", mannitol, xylitol, erythritol can be preferably mentioned, mannitol and erythritol are further preferably mentioned, and mannitol (particularly D-mannitol) can be particularly preferably mentioned. As erythritol, one generally produced by fermentation with yeast and the like using glucose as a starting material, and having a particle size of 50 mesh or below is used. The erythritol can be obtained as a commercially available product (manufactured by B Food Science Co., Ltd. etc.).

Examples of the aforementioned "excipient" include water-soluble sugar alcohol and, for example, crystalline cellulose, sodium carboxymethylcellulose, lactose, sucrose, starch, cornstarch, light anhydrous silicic acid, magnesium alumino metasilicate and the like. One kind of these excipients may be used singly or two or more kinds thereof may also be used in combination.

The content of the aforementioned "excipient" in the "outer layer" is generally about 30-about 90 wt %.

In the tablet of the present invention, the outer layer may contain a pH adjuster as an additive according to the kind of P-CAB. Where necessary, binder, lubricant, light shielding agent, colorant, disintegrant, corrigent, sweetener, flavor and the like may also be contained.

Examples of the aforementioned "pH adjuster" include organic acid and the like.

The aforementioned "organic acid" is preferably contained when P-CAB is an organic acid salt and the like of a compound exemplified as the aforementioned "Group A", and a highly nucleophilic compound having a primary or secondary amino group.

Examples of the organic acid include adipic acid, ascorbic acid, benzoic acid, oleic acid, succinic acid, acetic acid, tartaric acid, sorbic acid, fumaric acid, lactic acid, maleic acid, malonic acid, citric anhydride, maleic anhydride, phthalic anhydride, malic acid and the like. Of the organic acids, carboxylic acids such as fumaric acid, sorbic acid, maleic acid, oleic acid, succinic acid, tartaric acid and the like are preferably used, and fumaric acid, succinic acid, tartaric acid and the like more preferable, and fumaric acid is particularly preferable.

In P-CAB compounds having a primary or secondary amino group, these organic acids can prevent a reaction of an amino group with α or ß-unsaturated carbonyl compound, by which contribute to the stabilization of the preparation.

One kind of these organic acids may be used singly or two or more kinds thereof may also be used in combination.

In the tablet of the present invention, when the outer layer contains an organic acid, the content of the organic acid in the outer layer is generally 0.001-1.0 wt %, preferably 0.01-0.5 wt %.

In addition, the content ratio (weight ratio) of the organic acid to P-CAB is desirably P-CAB:organic acid=1:0.001-1:0.01.

Examples of the aforementioned "binder" include hydroxypropylcellulose, hydroxypropylmethylcellulose, crystalline cellulose, pregelatinized starch, polyvinylpyrrolidone, gum arabic powder, gelatin, pullulan, low-substituted hydroxypropylcellulose and the like.

The content of the aforementioned "binder" in the outer layer is generally about 1-about 15 wt %.

Examples of the aforementioned "lubricant" include talc, magnesium stearate, sucrose fatty acid ester, glycerol fatty acid ester, polyethylene glycol, stearic acid, hydrogenated oil and the like.

The content of the aforementioned "lubricant" in the outer layer is generally about 0.1-about 3 wt %.

Examples of the aforementioned "light shielding agent" include titanium oxide ($TiO_2$) and the like.

The content of the aforementioned "light shielding agent" in the outer layer is generally about 0-about 3 wt %.

Examples of the aforementioned "colorant" include food colors such as Food Color Yellow No. 5, Food Color Red No. 2, Food Color Blue No. 2 and the like; food lake colors; coloration pigments such as yellow ferric oxide, red iron oxide and the like, and the like.

The content of the aforementioned "colorant" in the outer layer is generally about 0-about 3 wt %.

As the aforementioned "disintegrant", a disintegrant conventionally used in the pharmaceutical field can be used.

Examples thereof include (1) crospovidone (e.g., Kollidon CL-F (manufactured by BASF)), (2) a disintegrant called superdisintegrant such as croscarmellose sodium (manufactured by FMC-Asahi Kasei Corporation), carmellose calcium (manufactured by GOTOKU CHEMICAL CO., LTD.) and the like, (3) sodium carboxymethyl starch (e.g., manufactured by Matsutani Chemical Industry Co., Ltd.), (4) low-substituted hydroxypropylcellulose (e.g., manufactured by Shin-Etsu Chemical Co., Ltd.), (5) cornstarch and the like.

As the "crospovidone", any crosslinked polymer having a chemical name 1-ethenyl-2-pyrrolidinone homopolymer may be used including polyvinyl polypyrrolidone (PVPP) and 1-vinyl-2-pyrrolidinone homopolymer. Specific examples thereof include Kollidon CL (manufactured by BASF), Kollidon CL-F (manufactured by BASF), Polyplasdone XL (manufactured by ISP), Polyplasdone XL-10 (manufactured by ISP), Polyplasdone INF-10 (manufactured by ISP) and the like.

The content of the aforementioned "disintegrant" in the outer layer is generally 0-about 15 wt %.

Examples of the aforementioned "corrigent" include citric acid (citric anhydride), tartaric acid, malic acid and the like.

Examples of the aforementioned "sweetener" include saccharin sodium, dipotassium glycyrrhizinate, aspartame, stevia, thaumatin and the like.

The aforementioned "flavor" may be any of synthetic substances and naturally occurring substances and, for example, lemon, lime, orange, menthol, strawberry and the like can be mentioned.

In the tablet of the present invention, the "outer layer" is preferably a composition containing P-CAB; one or more kinds of excipient selected from the group consisting of water-soluble sugar alcohol such as mannitol, erythritol and the like, crystalline cellulose and carboxymethylcellulose; a binder such as hydroxypropylcellulose and the like; and a lubricant such as magnesium stearate and the like. Where necessary, a pH adjuster such as fumaric acid and the like may also be contained.

To impart shading function and/or moisture-proof function, or for bitter taste masking, the tablet of the present invention optionally further has a "coating layer" on the outside of the outer layer (hereinafter the "coating layer" is sometimes to be referred to as an "over-coating layer").

The over-coating layer contains one or more kinds selected from the group consisting of a water-soluble polymer and a lubricant.

Examples of the aforementioned "water-soluble polymer" include ethanol-soluble water-soluble polymer (e.g., cellulose derivative such as hydroxypropylcellulose (HPC) and the like, polyvinylpyrrolidone and the like), ethanol-insoluble water-soluble polymer (e.g., cellulose derivative such as hydroxypropylmethylcellulose (HPMC), methylcellulose, carmellose sodium and the like, sodium polyacrylate, poly(vinyl alcohol), sodium alginate, guar gum and the like) and the like. One kind of these water-soluble polymers may be used singly or two or more kinds thereof may also be used in combination.

As the water-soluble polymer, one or more kinds selected from the group consisting of hydroxypropylcellulose, poly(vinyl alcohol) and hydroxypropylmethylcellulose is/are preferable.

The content of the "water-soluble polymer" in the over-coating layer is generally about 30-about 90 wt %.

Examples of the aforementioned "lubricant" include talc, magnesium stearate, sucrose fatty acid ester, glycerol fatty acid ester, polyethylene glycol, stearic acid, hydrogenated oil and the like.

The content of the "lubricant" in the over-coating layer is generally about 5-about 40 wt %.

The over-coating layer may further contain a light shielding agent such as titanium oxide ($TiO_2$) and the like; a surfactant such as sodium lauryl sulfate, polysorbate (e.g., polysorbate 80), polyoxyethylene-polyoxypropylene copolymer and the like; and a dispersing agent such as glycerol fatty acid ester and the like.

Particularly, from the aspects of improvement of shading property and bitter taste masking of the tablet, the tablet of the present invention preferably has an over-coating layer, and the over-coating layer preferably contains the above-mentioned water-soluble polymer and light shielding agent.

The over-coating layer is formed by applying an over-coating solution obtained by dissolving or suspending a water-soluble polymer, a lubricant and the like in a solvent such as water and the like on the outer layer of the tablet of the present invention by a general coating method (e.g., a method for spraying the coating solution on the outer layer surface of the tablet of the present invention by using a film coating machine, a method for spray coating by a fluid bed coating method and the like).

(3) Production Method of the Tablet of the Present Invention

The tablet of the present invention can be produced by coating the "enteric-coated tablet containing acetylsalicylic acid" in the inner core with an intermediate layer when desired, and spraying a solution or suspension containing P-CAB by a method known per se.

The "solution or suspension containing P-CAB" is prepared by dissolving or suspending P-CAB and an excipient such as water-soluble sugar alcohol and the like, and an additive such as pH adjuster, binder, lubricant, light shielding agent and the like when desired in a solvent such as water and the like, and used as a coating solution for the outer layer. The aforementioned coating solution can be sprayed on the inner core tablet (enteric-coated tablet containing acetylsalicylic acid, or the aforementioned enteric-coated tablet containing acetylsalicylic acid and further coated with an intermediate layer) by a general method (e.g., method for spraying on a surface tablet by using a film coating machine, spray coating including fluid bed coating method and the like, and the like). Where necessary, moreover, a coating of the aforementioned over-coating layer may be formed on the outside of the outer layer.

In addition, the tablet of the present invention can also be produced by mixing P-CAB and an additive such as excipient and the like, adding, when desired, other additive such as binder and the like, granulating the mixture to give an outer layer granulated powder, then mixing with outer layer mixture component such as other excipient and the like to give an outer layer mixed powder, and tableting the outer layer mixed powder with the inner core tablet (enteric-coated tablet containing acetylsalicylic acid or the aforementioned enteric-coated tablet containing acetylsalicylic acid in which the intermediate layer is further coated).

For example, an additive such as binder, pH adjuster and the like is dissolved or suspended in a solvent such as water and the like to prepare a coating solution, which is sprayed on a mixture of P-CAB, and an excipient such as water-soluble sugar alcohol, crystalline cellulose and the like, and the mixture is granulated to give an outer layer granulated powder. Then, the aforementioned outer layer granulated powder, and other outer layer constituent component such as an excipient such as crystalline cellulose and the like, lubricant and the like are mixed to give an outer layer mixed powder. Then, the inner core tablet (enteric-coated tablet containing acetylsalicylic acid, or the aforementioned enteric-coated tablet containing acetylsalicylic acid in which the intermediate layer is further coated), and the aforementioned outer layer mixed powder are dry coated tableted, whereby the tablet of the present invention can be produced.

The tablet obtained by tableting may be further coated with the aforementioned over-coating layer, where necessary, on the outside of the outer layer.

The "mixing" in the aforementioned production step is performed by a mixing method generally used. The "mixing" is performed using an apparatus such as vertical granulator VG10 (manufactured by POWREX), fluid bed granulator LAB-1, FD-3S, FD-WSG-60 (all manufactured by POWREX), FLO-5 M (manufactured by Freund Corporation), V-type mixer, tumbler mixer and the like.

For production of an outer layer granulated powder, a granulation method such as a tumbling granulation method (e.g., centrifugation tumbling granulation method), a fluid granulation method, a stirring granulation method and the like is used.

The "dry coated tableting" is performed by single punch tableting using Autograph (manufactured by Shimadzu Corporation) and the like, or a rotary dry coated tableting machine (manufactured by Kikusui Seisakusho Ltd., or manufactured by HATA TEKKOSHO CO., LTD.) and the like.

After tableting, where necessary, "drying" may be applied. For drying, any method used for drying preparations in general may be employed, for example, vacuum drying, fluidized bed drying and the like.

The tablet of the above-mentioned present invention is useful as a lower toxic and safe combined use medicament of P-CAB and acetylsalicylic acid.

The tablet of the present invention can be orally administered to mammals (e.g., human, monkey, sheep, horse, dog, cat, rabbit, rat, mouse and the like) for the purpose of suppressing thrombus and/or embolization in cerebrovascular and circulatory diseases, treatment and prophylaxis of ulcer caused by non-steroidal anti-inflammatory agents; and the like.

The tablet of the present invention contains P-CAB. Therefore, it shows superior antiulcer activity, gastric acid secretion-inhibitory action, mucosa-protecting action, eradication aiding action of Helicobacter pylori and the like.

For eradication or aid of eradication of Helicobacter pylori, the tablet of the present invention, a penicillin antibiotic (e.g., amoxicillin and the like) and erythromycin antibiotic (e.g., clarithromycin and the like) may be used in combination.

Since the tablet of the present invention contains acetylsalicylic acid, it is useful as a prophylactic and/or therapeutic agent for cerebrovascular or circulatory diseases, for example, a thrombus and/or embolization inhibitor for angina pectoris (chronic stable angina pectoris, unstable angina pectoris), myocardial infarction; a prophylactic and/or therapeutic agent for ischemic cerebrovascular disorder (transient ischemic attack (TIA), cerebral infarction); a thrombus and/or embolization inhibitor used after coronary-artery bypass surgery (CABG) or percutaneous transluminal coronary angioplasty (PTCA); or a prophylactic and/or therapeutic agent for Kawasaki disease (including cardiovascular sequelae due to Kawasaki disease).

Therefore, the tablet of the present invention can be administered for the purpose of treating gastric ulcer or duodenal ulcer or suppressing the onset of these, while continuing the administration of acetylsalicylic acid. When prophylaxis and/or treatment of such diseases is desired, about 10 mg-about 40 mg of P-CAB is administered per day, and about 70 mg-about 120 mg of acetylsalicylic acid is administered per day (low dose).

In addition, acetylsalicylic acid can also be used as one kind of non-steroidal anti-inflammatory drug mainly for the treatment of pain, fever and inflammation. Non-steroidal anti-inflammatory drugs sometimes cause gastric ulcer or duodenal ulcer. Particularly, in the treatment of rheumatoid arthritis, osteoarthritis and the like, discontinuation of the administration of non-steroidal anti-inflammatory drugs is sometimes difficult since QOL of the patients markedly decreases. In such cases, the tablet of the present invention can be administered for the purpose of treating gastric ulcer or duodenal ulcer or suppressing the onset of these, while continuing the administration of a non-steroidal anti-inflammatory drug.

When such treatment is desired, about 10 mg-about 40 mg of P-CAB is administered per day, and about 240 mg-about 400 mg of acetylsalicylic acid is administered per day.

The daily dose of the tablet of the present invention is appropriately determined according to the level of symptoms, animal species, age, sex, body weight of the subject of administration, timing and interval of administration, the kind of the active ingredient and the like, and is not particularly limited. The tablet of the present invention may be administered once per day or in 2-3 divided doses.

Furthermore, the tablet of the present invention is superior in the dissolution property and preservation stability of the active ingredient (acetylsalicylic acid and P-CAB).

Particularly, in the tablet of the present invention, contact with water in acetylsalicylic acid as the active ingredient is prevented. Thus, hydrolysis thereof is prevented and the active ingredient shows high preservation stability.

While acetylsalicylic acid sometimes shows poor blending performance with P-CAB, the tablet of the present invention can further improve stability by forming an intermediate layer between the inner core and the outer layer and/or an over-coating layer on the outer layer.

EXAMPLES

While the present invention is explained in more detail by referring to the following Examples, the present invention is not limited to these Examples.

Example 1

Acetylsalicylic acid (granulation product: manufactured by Novacyl Rhodine 3118) (45045 g), cornstarch (4905 g), crystalline cellulose (CEOLUS PH-101 (trade name; manufactured by Asahi Kasei Corporation)) (2925 g) and carmellose (2925 g) were weighed and mixed in a tumbler mixer. This was tableted by a rotary tableting machine (manufactured by Kikusui Seisakusho Ltd.) using a φ7.0 mm R round punch to give core tablets (tablet weight 124 mg) of the inner core.

A 20 wt % aqueous polysorbate 80 solution (960 g) was dissolved in 21940 g of water, heated to 70° C., glycerol monostearate (488 g) was added, and the mixture was dispersed by a dispersion machine to give a glycerol monostearate dispersion. Thereto were added methacrylic acid copolymer LD (Eudragit L30D-55 (trade name; manufactured by Evonik)) (24290 g) (solid amount 7287 g), ethyl acrylate-methyl methacrylate copolymer (Eudragit NE30D (trade name; manufactured by Evonik)) (2696 g) (solid amount 808.8 g), citric anhydride (8 g) and triethyl citrate (1616 g) and the mixture was mixed to give an enteric coated solution. Using DRIACOATER (manufactured by POWREX), the aforementioned core tablets (60760 g) were coated with the aforementioned enteric coating solution to a solid component amount of an enteric coating layer of 13 mg per one tablet to give enteric-coated tablets containing acetylsalicylic acid (tablet weight 137 mg).

Hydroxypropylcellulose (189.0 g) was dissolved in 1188 g of water, talc (21.0 g) was added and the mixture was stirred by a stirring machine to give an intermediate layer coating solution. Using DRIACOATER (manufactured by POWREX), the aforementioned enteric-coated tablets (2740 g) containing acetylsalicylic acid were coated with the aforementioned intermediate layer coating solution to a solid component amount of an intermediate layer of 7.0 mg per one tablet to give inner core tablets (tablet weight 144.0 mg).

D-mannitol (1215 g), fumaric acid (3.3 g) and hydroxypropylcellulose (90.0 g) were dissolved in 11450 g of water, vonoprazan fumarate (402.0 g) was added, and the mixture was stirred by a stirring machine to give a coating solution containing vonoprazan fumarate. Using DRIACOATER (POWREX CORPORATION), the aforementioned inner core tablets (2880 g) were coated with the aforementioned coating solution containing vonoprazan fumarate to a solid component amount of an outer layer of 57.0 mg per one tablet to give dry coated tablets (tablet weight 201 mg).

Hydroxypropylmethylcellulose (135.0 g) and sterilized talc (27.0 g) were dissolved in 1458 g of water, titanium oxide (18.0 g) was added and the mixture was dispersed by a dispersion machine to give an over-coating solution. Using DRIACOATER (manufactured by POWREX), the aforementioned dry coated tablets (3980 g) were coated with the aforementioned over-coating solution to a solid component amount of an over-coating layer of 6.0 mg per one tablet to give the tablets of the present invention having the over-coating layer (tablet weight 207 mg).

Example 2

Acetylsalicylic acid (granulation product: manufactured by Novacyl Rhodine 3118) (57000 g), cornstarch (6270 g), crystalline cellulose (CEOLUS PH-101 (trade name; manufactured by Asahi Kasei Corporation)) (3705 g) and carmellose (3705 g) were weighed and mixed in a tumbler mixer. This was tableted by a rotary tableting machine (manufactured by Kikusui Seisakusho Ltd.) using a $\varphi$6.5 mm R round punch to give core tablets (tablet weight 124 mg) of the inner core.

A 20 wt % aqueous polysorbate 80 solution (960 g) was dissolved in 21940 g of water, heated to 70° C., glycerol monostearate (488 g) was added, and the mixture was dispersed by a dispersion machine to give a glycerol monostearate dispersion. Thereto were added methacrylic acid copolymer LD (Eudragit L30D-55 (trade name; manufactured by Evonik)) (24290 g) (solid amount 7287 g), ethyl acrylate-methyl methacrylate copolymer (Eudragit NE30D (trade name; manufactured by Evonik)) (2696 g) (solid amount 808.8 g), citric anhydride (8 g) and triethyl citrate (1616 g) and the mixture was mixed to give an enteric coated solution. Using DRIACOATER (manufactured by POWREX), the aforementioned core tablets (8680 g) were coated with the aforementioned enteric coating solution to a solid component amount of an enteric coating layer of 13 mg per one tablet to give enteric-coated tablets containing acetylsalicylic acid (tablet weight 137 mg).

Hydroxypropylcellulose (603.0 g) was dissolved in 3790 g of water, talc (67.0 g) was added and the mixture was stirred by a stirring machine to give an intermediate layer coating solution. Using DRIACOATER (manufactured by POWREX), the aforementioned enteric-coated tablets (9590 g) containing acetylsalicylic acid were coated with the aforementioned intermediate layer coating solution to a solid component amount of an intermediate layer of 6.7 mg per one tablet to give inner core tablets (tablet weight 143.7 mg).

Hydroxypropylcellulose (1350 g) and fumaric acid (16.5 g) were dissolved in 21150 g of water to give a 6 wt % aqueous hydroxypropylcellulose solution containing fumaric acid. Vonoprazan fumarate (960.9 g), D-mannitol (15450 g), crystalline cellulose (CEOLUS KG-1000 (trade name; manufactured by Asahi Kasei Corporation)) (2160 g) and sodium carboxymethylcellulose (1080 g) were weighed and the aforementioned 6 wt % aqueous hydroxypropylcellulose solution (10808 g) containing fumaric acid was sprayed in a fluid bed granulator (manufactured by POWREX, FD-WGS-30) to give a granulated powder. Crystalline cellulose (CEOLUS KG-1000 (trade name; manufactured by Asahi Kasei Corporation)) (1050 g), magnesium stearate (210 g) and the aforementioned granulated powder (19740 g) were mixed by a tumbler mixer to give an outer layer mixed powder.

The aforementioned inner core tablet (3593 g) and the aforementioned outer layer mixed powder (7500 g) were dry coated tableted (rotating speed 15 rpm, tableting pressure 8 kN) by a rotary dry coated tableting machine (manufactured by HATA TEKKOSHO CO., LTD.) using a diameter 10 mm R round punch. Dry coated tablets having a tablet weight of 443.7 mg per tablet (weight constituent; inner core tablet 143.7 mg, outer layer 300 mg) were obtained.

Hydroxypropylmethylcellulose (471.2 g) and sterilized talc (64.0 g) were dissolved in 5377 g of water, titanium oxide (116.8 g) was added and the mixture was dispersed by a dispersion machine to give an over-coating solution. Using DRIACOATER (manufactured by POWREX), the aforementioned dry coated tablets (8874 g) were coated with the aforementioned over-coating solution to a solid component amount of an over-coating layer of 16.3 mg per one tablet to give the tablets of the present invention having the over-coating layer (tablet weight 460 mg).

Example 3

Acetylsalicylic acid (granulation product: manufactured by Novacyl Rhodine 3118) (45045 g), cornstarch (4905 g), crystalline cellulose (CEOLUS PH-101 (trade name; manufactured by Asahi Kasei Corporation)) (2925 g) and carmellose (2925 g) were weighed and mixed in a tumbler mixer. This was tableted by a rotary tableting machine (manufactured by Kikusui Seisakusho Ltd.) using a $\varphi$7.0 mm R round punch to give core tablets (tablet weight 124 mg) of the inner core.

A 20 wt % aqueous polysorbate 80 solution (960 g) was dissolved in 21940 g of water, heated to 70° C., glycerol monostearate (488 g) was added, and the mixture was dispersed by a dispersion machine to give a glycerol monostearate dispersion. Thereto were added methacrylic acid copolymer LD (Eudragit L30D-55 (trade name; manufactured by Evonik)) (24290 g) (solid amount 7287 g), ethyl acrylate-methyl methacrylate copolymer (Eudragit NE30D (trade name; manufactured by Evonik)) (2696 g) (solid amount 808.8 g), citric anhydride (8 g) and triethyl citrate (1616 g) and the mixture was mixed to give an enteric coated solution. Using DRIACOATER (manufactured by POW- REX), the aforementioned core tablets (60760 g) were coated with the aforementioned enteric coating solution to a solid component amount of an enteric coating layer of 13 mg per one tablet to give enteric-coated tablets containing acetylsalicylic acid (tablet weight 137 mg).

Hydroxypropylcellulose (189.0 g) was dissolved in 1188 g of water, talc (21.0 g) was added and the mixture was stirred by a stirring machine to give an intermediate layer coating solution. Using DRIACOATER (manufactured by POWREX), the aforementioned enteric-coated tablets (2740 g) containing acetylsalicylic acid were coated with the aforementioned intermediate layer coating solution to a solid component amount of an intermediate layer of 7.0 mg per one tablet to give inner core tablets (tablet weight 144.0 mg).

D-mannitol (1218 g) and hydroxypropylcellulose (90.0 g) were dissolved in 11450 g of water, vonoprazan fumarate (402.0 g) was added, and the mixture was stirred by a stirring machine to give a coating solution containing vonoprazan fumarate. Using DRIACOATER (POWREX CORPORATION), the aforementioned inner core tablets (2880 g) were coated with the aforementioned coating solution containing vonoprazan fumarate to a solid component amount of an outer layer of 57.0 mg per one tablet to give dry coated tablets (tablet weight 201 mg).

Hydroxypropylmethylcellulose (135.0 g) and sterilized talc (27.0 g) were dissolved in 1458 g of water, titanium oxide (18.0 g) was added and the mixture was dispersed by a dispersion machine to give an over-coating solution. Using DRIACOATER (manufactured by POWREX), the aforementioned dry coated tablets (3980 g) were coated with the aforementioned over-coating solution to a solid component amount of an over-coating layer of 6.0 mg per one tablet to give the tablets of the present invention having the over-coating layer (tablet weight 207 mg).

Example 4

Acetylsalicylic acid (granulation product: manufactured by Novacyl Rhodine 3118) (45045 g), cornstarch (4905 g), crystalline cellulose (CEOLUS PH-101 (trade name; manufactured by Asahi Kasei Corporation)) (2925 g) and carmellose (2925 g) were weighed and mixed in a tumbler mixer. This was tableted by a rotary tableting machine (manufactured by Kikusui Seisakusho Ltd.) using a φ7.0 mm R round punch to give core tablets (tablet weight 124 mg) of the inner core.

A 20 wt % aqueous polysorbate 80 solution (960 g) was dissolved in 21940 g of water, heated to 70° C., glycerol monostearate (488 g) was added, and the mixture was dispersed by a dispersion machine to give a glycerol monostearate dispersion. Thereto were added methacrylic acid copolymer LD (Eudragit L30D-55 (trade name; manufactured by Evonik)) (24290 g) (solid amount 7287 g), ethyl acrylate-methyl methacrylate copolymer (Eudragit NE30D (trade name; manufactured by Evonik)) (2696 g) (solid amount 808.8 g), citric anhydride (8 g) and triethyl citrate (1616 g) and the mixture was mixed to give an enteric coated solution. Using DRIACOATER (manufactured by POWREX), the aforementioned core tablets (60760 g) were coated with the aforementioned enteric coating solution to a solid component amount of an enteric coating layer of 13 mg per one tablet to give enteric-coated tablets containing acetylsalicylic acid (tablet weight 137 mg).

Hydroxypropylcellulose (189.0 g) was dissolved in 1188 g of water, talc (21.0 g) was added and the mixture was stirred by a stirring machine to give an intermediate layer coating solution. Using DRIACOATER (manufactured by POWREX), the aforementioned enteric-coated tablets (2740 g) containing acetylsalicylic acid were coated with the aforementioned intermediate layer coating solution to a solid component amount of an intermediate layer of 7.0 mg per one tablet to give inner core tablets (tablet weight 144.0 mg).

D-mannitol (1218 g) and hydroxypropylcellulose (90.0 g) were dissolved in 11450 g of water, vonoprazan fumarate (402.0 g) was added, and the mixture was stirred by a stirring machine to give a coating solution containing vonoprazan fumarate. Using DRIACOATER (POWREX CORPORATION), the aforementioned inner core tablets (2880 g) were coated with the aforementioned coating solution containing vonoprazan fumarate to a solid component amount of an outer layer of 57.0 mg per one tablet to give dry coated tablets (tablet weight 201 mg).

Hydroxypropylmethylcellulose (135.0 g) and sterilized talc (27.0 g) were dissolved in 1458 g of water, titanium oxide (18.0 g) was added and the mixture was dispersed by a dispersion machine to give an over-coating solution. Using DRIACOATER (manufactured by POWREX), the aforementioned dry coated tablets (3980 g) were coated with the aforementioned over-coating solution to a solid component amount of an over-coating layer of 6.0 mg per one tablet to give the tablets of the present invention having the over-coating layer (tablet weight 207 mg).

Example 5

Acetylsalicylic acid (granulation product: manufactured by Novacyl Rhodine 3118) (45045 g), cornstarch (4905 g), crystalline cellulose (CEOLUS PH-101 (trade name; manufactured by Asahi Kasei Corporation)) (2925 g) and carmellose (2925 g) were weighed and mixed in a tumbler mixer. This was tableted by a rotary tableting machine (manufactured by Kikusui Seisakusho Ltd.) using a φ7.0 mm R round punch to give core tablets (tablet weight 124 mg) of the inner core.

A 20 wt % aqueous polysorbate 80 solution (960 g) was dissolved in 21940 g of water, heated to 70° C., glycerol monostearate (488 g) was added, and the mixture was dispersed by a dispersion machine to give a glycerol monostearate dispersion. Thereto were added methacrylic acid copolymer LD (Eudragit L30D-55 (trade name; manufactured by Evonik)) (24290 g) (solid amount 7287 g), ethyl acrylate-methyl methacrylate copolymer (Eudragit NE30D (trade name; manufactured by Evonik)) (2696 g) (solid amount 808.8 g), citric anhydride (8 g) and triethyl citrate (1616 g) and the mixture was mixed to give an enteric coated solution. Using DRIACOATER (manufactured by POWREX), the aforementioned core tablets (60760 g) were coated with the aforementioned enteric coating solution to a solid component amount of an enteric coating layer of 13 mg per one tablet to give inner core tablets (tablet weight 137 mg).

D-mannitol (1215 g), fumaric acid (3.3 g) and hydroxypropylcellulose (90.0 g) were dissolved in 11450 g of water, vonoprazan fumarate (402.0 g) was added, and the mixture was stirred by a stirring machine to give a coating solution containing vonoprazan fumarate. Using DRIACOATER (POWREX CORPORATION), the aforementioned inner core tablets (2740 g) were coated with the aforementioned coating solution containing vonoprazan fumarate to a solid component amount of an outer layer of 57.0 mg per one tablet to give dry coated tablets (tablet weight 194 mg).

Poly(vinyl alcohol) (592 g), sterilized talc (496 g), titanium oxide (400 g), sodium lauryl sulfate (48 g) and glycerol fatty acid ester (64 g) were added to 9070 g of water, and the mixture was dissolved by stirring to give an over-coating solution. Using DRIACOATER (manufactured by POWREX), the aforementioned dry coated tablets (3840 g) were coated with the aforementioned over-coating solution to a solid component amount of an over-coating layer of 16.0 mg per one tablet to give the tablets of the present invention having the over-coating layer (tablet weight 210 mg).

The formulations of the preparations of Examples 1-5 are shown in the following Table 1.

INDUSTRIAL APPLICABILITY

As described in detail above, the tablet of the present invention is useful as a combined use medicament of P-CAB and acetylsalicylic acid.

The tablet of the present invention may be used for the treatment of gastric ulcer or duodenal ulcer, or suppressing the onset of these while continuing the administration of acetylsalicylic acid for the prophylaxis and/or treatment of

TABLE 1

| component name | Ex. 1 formulation amount (mg per tablet) | Ex. 2 formulation amount (mg per tablet) | Ex. 3 formulation amount (mg per tablet) | Ex. 4 formulation amount (mg per tablet) | Ex. 5 formulation amount (mg per tablet) |
| --- | --- | --- | --- | --- | --- |
| acetylsalicylic acid (Rhodine 3118) | 100.0 | 100.0 | 100.0 | 100.0 | 100.0 |
| cornstarch | 11.0 | 11.0 | 11.0 | 11.0 | 11.0 |
| crystalline cellulose (PH-101) | 6.5 | 6.5 | 6.5 | 6.5 | 6.5 |
| carmellose | 6.5 | 6.5 | 6.5 | 6.5 | 6.5 |
| subtotal (mg) of core tablet in inner core | 124.0 | 124.0 | 124.0 | 124.0 | 124.0 |
| methacrylic acid copolymer LD (solid content) (Eudragit L30D-55) | 9.11 | 9.11 | 9.11 | 9.11 | 9.11 |
| ethyl acrylate-methyl methacrylate copolymer (solid content) (Eudragit NE30D) | 1.01 | 1.01 | 1.01 | 1.01 | 1.01 |
| polysorbate 80 | 0.24 | 0.24 | 0.24 | 0.24 | 0.24 |
| glycerol monostearate | 0.61 | 0.61 | 0.61 | 0.61 | 0.61 |
| citric anhydride | 0.01 | 0.01 | 0.01 | 0.01 | 0.01 |
| triethyl citrate | 2.02 | 2.02 | 2.02 | 2.02 | 2.02 |
| subtotal (mg) of enteric-coated tablet containing acetylsalicylic acid | 137.0 | 137.0 | 137.0 | 137.0 | 137.0 |
| hydroxypropyl-cellulose | 6.30 | 6.03 | 6.30 | | |
| hydroxypropyl-methylcellulose | | | | 6.30 | |
| sterilized talc | 0.70 | 0.67 | 0.70 | 0.70 | |
| inner core tablet subtotal (mg) | 144.0 | 143.7 | 144.0 | 144.0 | 137.0 |
| vonoprazan fumarate | 13.36 | 13.36 | 13.36 | 13.36 | 13.36 |
| hydroxypropyl-cellulose | 3.00 | 9.00 | 3.00 | 3.00 | 3.00 |
| D-mannitol | 40.53 | 214.53 | 40.64 | 40.64 | 40.53 |
| fumaric acid | 0.11 | 0.11 | | | 0.11 |
| crystalline cellulose (KG-1000) | | 45.00 | | | |
| sodium carboxymethyl starch | | 15.00 | | | |
| magnesium stearate | | 3.00 | | | |
| dry coated tablet subtotal (mg) | 201.0 | 443.7 | 201.0 | 201.0 | 194.0 |
| hydroxypropyl-methylcellulose | 4.5 | 11.78 | 4.5 | 4.5 | |
| sterilized talc | 0.9 | 1.60 | 0.9 | 0.9 | 4.96 |
| titanium oxide | 0.5 | 2.92 | 0.6 | 0.6 | 4.00 |
| poly(vinyl alcohol) | | | | | 5.92 |
| sodium lauryl sulfate | | | | | 0.48 |
| glycerol fatty acid ester | | | | | 0.64 |
| total | 207.0 | 460.0 | 207.0 | 207.0 | 210.0 | cerebrovascular and circulatory diseases, or for the treatment of pain, fever, inflammation.

This application is based on a patent application No. 2015-151336 filed in Japan, the contents of which are incorporated in full herein.

The invention claimed is:

1. A tablet comprising an inner core and an outer layer, wherein the inner core is an enteric-coated tablet comprising acetylsalicylic acid, and the outer layer comprises a potassium-competitive acid blocker (P-CAB) wherein the outer layer is free of enteric coating, and
   wherein the outer layer further comprises fumaric acid, and
   wherein the content ratio of the P-CAB and the fumaric acid (P-CAB:fumaric acid) is 1:0.001 to 1:0.01 in a weight ratio.

2. The tablet according to claim 1 wherein the potassium-competitive acid blocker is 1-[5-(2-fluorophenyl)-1-(pyridin-3-ylsulfonyl)-1H-pyrrol-3-yl]-N-methylmethanamine (vonoprazan) or a salt thereof.

3. The tablet according to claim 1 wherein the content of acetylsalicylic acid is 70 mg-120 mg per one table.

4. The tablet according to claim 1 comprising an intermediate layer between the inner core and the outer layer.

5. The tablet according to claim 4 wherein the intermediate layer comprises a water-soluble polymer.

6. The tablet according to claim 5 wherein the water-soluble polymer is one or more kinds selected from the group consisting of hydroxypropylcellulose, poly(vinyl alcohol) and hydroxypropylmethylcellulose.

7. The tablet according to claim 1 further comprising a coating layer on the outside of the outer layer.

8. The tablet according to claim 7 wherein the coating layer comprises a water-soluble polymer.

9. The tablet according to claim 8 wherein the water-soluble polymer is one or more kinds selected from the group consisting of hydroxypropylcellulose, poly(vinyl alcohol) and hydroxypropylmethylcellulose.

10. The tablet according to claim 1 wherein the enteric coating layer in the inner core comprises methacrylic acid copolymer LD and ethyl acrylate-methyl methacrylate copolymer.

11. The tablet according to claim 10 wherein the content ratio of methacrylic acid copolymer LD and ethyl acrylate-methyl methacrylate copolymer (methacrylic acid copolymer LD:ethyl acrylate-methyl methacrylate copolymer) is 85:15-95:5 in a weight ratio.

12. A method for producing the tablet according to claim 1 comprising spraying a solution or suspension comprising a potassium-competitive acid blocker on an enteric-coated tablet comprising acetylsalicylic acid.

13. A method for producing the tablet according to claim 4 comprising coating an enteric-coated tablet containing acetylsalicylic acid with an intermediate layer and thereafter spraying thereon a solution or suspension comprising a potassium-competitive acid blocker.

* * * * *